United States Patent [19]

Weinstock

[11] 4,160,765

[45] Jul. 10, 1979

[54] METHOD FOR 6-BROMINATION OF 1-PHENYL-2,3,4,5-TETRAHYDRO-1H-3-BENZAZEPINE COMPOUNDS

[75] Inventor: Joseph Weinstock, Phoenixville, Pa.

[73] Assignee: SmithKline Corporation, Philadelphia, Pa.

[21] Appl. No.: 742,965

[22] Filed: Nov. 17, 1976

[51] Int. Cl.² ............................................. C07D 223/16
[52] U.S. Cl. ........................ 260/239 BB; 260/340.6; 260/340.9 R; 424/244
[58] Field of Search ......................... 260/239 BB, 694; 424/244

[56] References Cited

FOREIGN PATENT DOCUMENTS 555831 2/1967 Switzerland ...................... 260/239 BB
1118688 6/1968 United Kingdom .............. 260/239 BB
1225053 3/1971 United Kingdom .............. 260/239 BB

OTHER PUBLICATIONS

Fuson, "Adv. Org. Chem." pp. 287–289, Wiley, N.Y., (1950).

*Primary Examiner*—Donald G. Daus
*Assistant Examiner*—D. B. Springer
*Attorney, Agent, or Firm*—William H. Edgerton

[57] ABSTRACT

The preparation of 6-bromo-7,8-dimethoxy-1-phenyl-2,3,4,5-tetrahydro-1H-3-benzazepines is described by direct bromination of the nucleus.

1 Claim, No Drawings

METHOD FOR 6-BROMINATION OF 1-PHENYL-2,3,4,5-TETRAHYDRO-1H-3-BENZAZEPINE COMPOUNDS

This invention comprises a new group of compounds which are 1-phenyl-2,3,4,5-tetrahydro-1H-3-benzazepines having at least three substituents in the benz-ring of the nucleus, one of which is a halo or halo-containing group substituted at the 6-position. These compounds have utility as medicinally active compounds especially as diuretic and/or cardiovascular agents due to their peripheral dopaminergic activity. They also demonstrate activity in animal tests which are known to predict anti-Parkinsonism activity by means of activity at the central dopamine receptors. Generally speaking therefore they have both potent peripheral or central dopaminergic activity.

The structure of the compounds of this invention are specifically identified by having a halo that is a chloro, bromo, iodo or fluoro or halo-containing substituent such as a trifluoromethyl or trifluoroethyl group at the 6-position of the 1-phenyltetrahydro-3-benzazepine system. Exemplary of this new group of compounds are those represented by the following structural formulas:

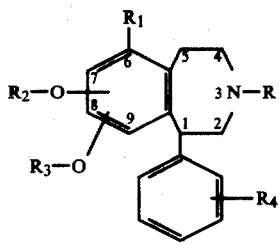

I in which:

R is H, benzyl, lower alkanoyl of from 1-5 carbons such as formyl, acetyl or trifluoroeactyl, lower alkyl of 1-5 carbon atoms, hydroxyethyl or lower alkenyl of 3-5 carbon atoms;

$R_1$ is halor or trifluoromethyl;

$R_2$ and $R_3$ are each hydrogen, lower alkyl of 1-5 carbon atoms, lower alkanoyl of 2-5 carbon atoms or, when taken together, methylene or ethylene; and $R_4$ is H, trifluoromethyl, halo such as F, Cl or Br, methyl, methoxy or hydroxy.

$R_2O$ and $R_3O$ are preferably hydroxy radicals at the 7,8 positions for maximal biological activity.

A subgeneric group of compounds within the above illustrative generic group are those of Formula I in which:

R is H;

$R_2$ and $R_3$ are the same and are hydrogen, methyl or acetyl with $R_2O$ and $R_3O$ being at the 7 and 8 positions respectively; and $R_4$ is H or hydroxy preferably in the meta or para position.

Individual compounds of note are those of Formula II

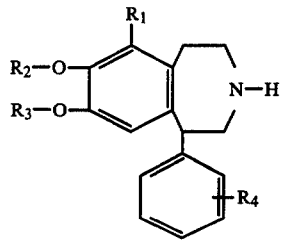

II in which:
$R_1$ is Cl or Br;
$R_2$ and $R_3$ are the same and are hydrogen; and
$R_4$ is hydrogen or m or p- OH.

The compounds of this invention may also have a fourth benz substituent such as at the 9 position but these are of no particular additional advantage from the viewpoint of their biological utility. The compounds in which $R_2$ and $R_3$ form an alkylene chain such as the methylenedioxy-containing compounds at the 7,8-positions are of primary interest as intermediates. Methylenedioxy-3-benzazepines in another series are reported in U.S. Pat. No. 3,795,683.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bismethylenesalicyclic, methanesulfonic ethanedisulfonic, acetic, oxalic, propionic, tartaric, salicyclic, citric, gluconic, aspartic, stearic, palmitic, itaconic, glycolic, p-aminobenzoic, glutamic, benzensulfonic, hydrochloric, hydrobromic, sulfuric, cyclohexylsulfamic, phosphoric and nitric acids. Similarly the quarternary salts include those prepared from organic halides such as methyl, iodide, ethyl iodide, benzyl chloride and the like.

Certain 1-phenyl-2,3,4,5-tetrahydro-1H-3-benzazepines have been described in U.S. Pat. No. 3,393,192; British Patent Specification No. 1,118,688; and Swiss Patent No. 555,831, including general methods of preparation. However these references disclose no benz-trisubstituted compounds, no 6-substituted compounds of any kind and no advantage to 6-halo substitution in the structures.

In an earlier filed still pending application Ser. No. 592,708 filed July 2, 1975 6-chloro-8,9-dimethoxy1-phenyl-2,3,4,5-tetrahydro-1H-3-benzazepine was described along with its use as an intermediate for preparing other end product benzazepines used as dopaminergic ingredients in the invention claimed in that application. The synthetic procedures and the use of that product as an intermediate were supplied by this applicant. The 8,9-disubstituted compounds are relatively less active biologically than the 7,8-disubstituted compounds which are an important subgeneric group of this invention as disclosed above.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Unless otherwise specified herein or in the claims, it is intended to include all isomers, whether separated or mixtures thereof. Where isomers are separated, the desired pharmacological activity will usually predominate in one of the isomers.

The compounds of Formula I in which R is hydrogen are generally prepared from intermediates of the following formula:

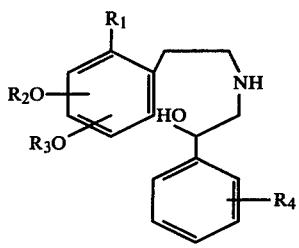

in which $R_1$ is halo or trifuoromethyl; $R_2$ and $R_3$ are lower alkyl or together are methylene; and $R_4$ is hydrogen or a chemically inert substituent of the group described above, by means of an intra-molecular cyclization effected by reaction with a reagent such as sulfuric acid alone or mixed with suitable solvents such as trifluroroacetic acid, polyphosphoric acid or a similar dehydrating agent.

Mixed alkoxy substituted compounds are prepared by selecting the proper phenethylamine starting material. To obtain the benzazepine products wherein $R_2$ and $R_3$ are hydrogen, cyclization of the corresponding methoxy substituted intermediates may be carried out with 48% hydrobromic acid at reflux temperature for from two to four hours whereby simultaneous demthylation of the methoxy groups occurs.

The phenethylamines (IV) which are used as starting materials for this method are either known or are prepared by methods described in U.S. Pat. No. 3,211,792, Chem. Abst. 80, 95398, U.S. Pat. No. 3,869,474, U.S. Pat. No. 3,804,839 or in the illustrative examples herein disclosed.

Alternatively, the compounds of Formula I where R is hydrogen may be prepared from 1-phenyl-2-oxo-2,3,4,5-tetrahydro-1H-3-benzazepine intermediates which are obtained by heating an appropriate phenylalkylamine with an ester of mandelic acid to give the amide. The latter is then cyclized to form the 2-oxobenzazepine intermediates which are chemically reduced, for example with borane in tetrahydrofuran, to the 1-phenyl-3-benzazepine products.

The compounds in which $R_1$ is bromo and $R_2$, $R_3$, $R_4$ and R contain only chemically inert groups can surprisingly by prepared by direct bromination at the 6-position of their chemical structures in excellent yields. This reaction is carried out most conveniently using about two mole equivalents of bromine in a suitable solvent such as acetic acid at about room or ambient temperature. The yield of the product in which $R_1$ is bromo, $R_2O-$ and 7,8-dimethoxy and R and $R_1$ are hydrogen is 70-85%. The product separates from the bromination mixture as a complex with one mole of bromine. The complexed bromine is eliminated easily by treatment with methanol/acetone.

The 6-bromo containing compound may optionally serve as an intermediate in a number of ways such as for preparing the 6-chloro or 6-iodo congeners as described in the Examples. The 6-bromo compound is also useful for preparing 6-lithium or Grignard intermediates. These can be reacted with a number of conventional reactants to introduce 6-substituents such as with iodine or hexachloroethane to introduce other halo substituents. The lithium salts are a part of this invention.

To prepare the compounds of Formula I where R is hydroxyethyl, lower alkyl or alkenyl, the corresponding benzazepines wherein R is hydrogen are alkylated by standard methods with ethylene oxide, a reactive lower alkyl halide such as the bromide or chloride or a reactive alkenyl halide such as an allyl bromide or chloride. Advantageously, to obtain the products where $R_2$ and/or $R_3$ are hydrogen the reaction with the alkylating agent is carried out in the corresponding methoxy substituted benzazepines in an inert solvent such as methanol or acetone, preferably at reflux temperature and in the presence of a basic condensing agent such as potassium hydroxide or carbonate. Treatment of the resulting product with, for example, boron tribromide or other ether splitting agents gives the active hydroxy substituted benzazepines.

The compounds of Formula I where R is methyl are conveniently prepared from methoxy substituted benzazepines wherein R is hydrogen by reaction with formic acid/formaldehyde. Treatment of the resulting product with boron tribromide gives the corresponding hydroxy substituted benzazepines.

To prepare the compounds of Formula I where $R_1$ or $R_2$ is alkanoyl, the corresponding 3-benzyl-dihydroxy-3-benzazepine (obtained by N-alkylation of the hydroxybenzazepine with benzyl bromide in the presence of potassium carbonate) is treated with the appropriate alkanoic acid anhydride or chloride, for example acetic anhydride, and the resulting alkanoyloxy substituted benzazepine is then hydrogenated in the presence of palladium-on-carbon to remove the protective benzyl group. The dialkanoyloxy derivatives such as the important 7,8-diacetoxy compounds can also be prepared by direct O-acylation of the 6-halo-7,8-dihydroxy-1-phenyl-2,3,4,5-tetrahydro-1H-3-benzazepine hydrobromide in trifluoroacetic acid at ambient temperature with the anhydride or halide. The N or 3-lower alkanoyl congeners in the dihydroxy series are prepared conveniently by N-acylating the methylenedioxy derivative followed by splitting the protective group. Also direct N-alkanoylation of the dihydroxy compounds is possible under controlled conditions and quantities of reactants as known to the art. As noted in the illustrative examples any O-acylation may necessitate a mild hydrolsis treatment.

The intermediates of Formula III above are conveniently prepared by heating equimolar amounts of a styrene oxide with a 3.4-dialkoxyphenethylamine which is either knonw or prepared by methods known to the art, each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivatives from sodium hydride and trimethylsulfonium iodide with the appropriately substituted benzaldehyde.

The active dopaminergic compounds of this invention used herein stimulate peripheral dopamine receptors, for example they increase renal blood flow and have as an end result hypotensive activity. This renal vasodilator activity of the benzazepine compounds of Formula I is measured in an anesthetized dog. In this pharmacological procedure, a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. Representative advantageous compounds of Formula I, 7,8-dihydroxy-1-phenyl-2,3,4,5-tetrahydro-1H-3-benzazepine substituted at the 6-position by chloro or bromo, tested by i.v. infusion as described above produced an $ED_{15}$ of 3.5 and 22 (9) mcg/kg respectively with little direct effect on systemic blood pressure in normotensive animals. $ED_{15}$ therefore is the cumulative dose by infusion which produces a 15% decrease in renal vascular resistance $$(R = \frac{\text{B.P. in mm/hg}}{\text{B.F. ml/min}}).$$

As a renal vasodilator in the anesthetized dog this 6-chloro compound was 10 times more efficacious than its 6-deschloro congener. Another very active compound, 6-chloro-7,8-dihydroxy-1-p-hydroxyphenyl-2,3,4,5-tetrahydro-1H-3-benzazepine gave a 26% decrease in renal resistance and at 29% increase in renal blood flow at a cumulative dose of 30 mcg/kg.

The compounds of this invention unexpectedly also cause a separation of side effects in dogs such as those caused by pressor reactions due to norepinephrine compared with the $ED_{15}$ cardiovascular dose as described above. Here the above 6-chloro and 6-bromo-7,8-dihydroxy compounds have a separation ratio of 1233 and >1388 respectively compared with their deshalo congener (47).

In addition to the renal vasodilator activity via a dopaminergic effect, certain benzazepine compounds of Formula I produce weak diuretic activity. Such diuretic activity is measured in the standard saline-loaded rat procedure. A test compound is administered i.p. at doses of from 10 to 40 mg/kg and the parameters measured are urine volume (hourly for three hours) plus sodium and potassium ion concentrations. Also conventional diuretic tests in the dog may be used. 6-Chloro-7,8-dihdroxy-1-phenyl-2,3,4,5-tetrahydro-1H-3-benzazepine tested in the phosphate mannitol dog produced a significant increase in renal plasma flow and natriuresis at a dose as low as 5 and 10 micrograms μg/kg/min i.v. Similar results were obtained at oral doses of 10 mg/kg (renal blood flow only). The 6-chloro-7,8-diacetoxy congener has better activity after oral absorption than does its 7,8-dihydroxy parent.

The benzazepine compounds of Formula I also have antiparkinsonism activity due to central dopaminergic activity as demonstrated by employing a modified standard animal pharmacological test procedure reported by Ungerstedt et al.; in *Brain Research* 24, 1970, 485–493. This procedure is based on a drug induced rotation of rats having extensive unilateral lesions of the substantia nigra. Briefly, the test comprises the quantitative recording of rotational behavior in rats in which 6-hdroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rate turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

Once again advantageous compounds of Formula I, 7-chloro or 7-bromo-7,8-dihydroxy-1-phenyl-2,3,4,5-tetrahydro-1H-3-benzazepines when tested as described above in rats produced $ED_{500}$, i.p. of 0.3 and 0.27 mg/kg respectively. As such they are both about 4 times as active as is the deshalo congener in this test. Further the compounds do not induce emesis or sterotyped behavior at doses which are effective in the rat turning model.

The same 6-bromo compound showed greater renal plasma flow (RPF) in the rat clearance test than did the desbromo congener. At 15 μg/kg/min. the RPF increased 60% over control with 85% increase in urine volume. The 6-chloro compound also increased volume 80%, RPF 48% and sodium ion excretion. Therefore these compounds demonstrate stronger diuretic properties than does their 6-hydrogen congener.

The pharmaceutical compositions of this invention having dopaminergic activity are prepared in conventional dosage unit forms by incorporating a compound of Formula I, an isomer or a pharmaceutically acceptable acid addition salt thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 15 mg to about 1000 mg of active ingredient per dosage unit but this quantity depends on the specific biological activity desired and the conditions of patient. Generally speaking lower doses are needed to stimulate central dopamine receptors than peripheral receptors.

The pharmaceutical carrier employed may be, for example, either a solid or liquid. Exemplary of solid carriers are lactose, terra alba, sucrose talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The methodof producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as two or three times a day with the daily dosage regimen being selected from about 50 mg to about 2 g. When the method described above is carried out hypotensive, diuretic or anti-parkinsonism, activity is produced with a minimum of side effects.

The following examples are designed solely to illustrate the preparation and use of the compounds of this invention. The temperatures are Centigrade. Other variations of these examples will be obvious to those skilled in the art.

EXAMPLE 1

A mixture of 100 g (0.55 mol) of 3,4-dimethoxyphenylethylamine and 66.2 g (0.55 mol) of styrene oxide in 200 ml of tetrahydrofuran was refluxed overnight. The solvent was removed in vacuo. About 500 ml of n-butyl chloride was added to the residue and the mixture cooled slightly. Filtration furnished N-[2-(3,4-dimethoxyphenyl)ethyl]-2-phenyl-2-hydroxyethylamine, m.p. 92°–93°.

The above prepared phenethylamine, 71.5 g (0.238 mol), was dissolved in 400 ml of acetic acid and the solution was cooled. To this solution was added 16.9 g (0.238 mol) of chlorine gas over a 30 to 45 minute period. The reaction mixture was poured into water, made basic with 40% sodium hydroxide solution and about 250 ml of ether added to the stirred solution. The resulting solid was filtered to give N-[2-(2-chloro-4,5-dimethoxyphenyl)ethyl]-2-phenyl-2-hydroxyethylamine, m.p. 110°–113°.

To 100 ml of concentrated sulfuric acid was added the above phenethylamine (10 g, 30 mmol) with stirring. After about 20 minutes the reaction mixture was poured over ice and extracted with ethyl acetate. The aqueous solution was made basic with sodium hydroxide pellets and 40% sodium hydroxide solution. The oil which forms was extracted with ether, the extract was dried and concentrated to about one-half volume. Ethereal hydrogen chloride was added to furnish 6-chloro-8,9-dimethoxy-1-phenyl-2,3,4,5-tetrahydro-1H-3-benzazepine hydrochloride, m.p. 209°–210°.

Heating the dimethoxy compound in an excess of 48% hydrobromic acid at reflux for 2 hours and cooling gives the 8,9-dihydroxy congener as the hydrobromide.

EXAMPLE 2

Isovanillin (200 g, 1.32 mole) was suspended in 1200 cc chloroform. Chlorine (103 g, 1.45 mole) was added by means of 3 500 cc portions of carbon tetrachloride, in which it was dissolved. The suspension was stirred vigorously during the addition and the reaction was kept around 25° by a water bath. The suspension was stirred for 22 minutes after the completion of the addition of chlorine. The precipitate was filtered and crystallized from methanol, then recrystallized from isopropanol/ethyl acetate. Yield 98.7 g (40%, m.p. 204°–206°) of 2-chloro-3-hydroxy-4-methoxybenzaldehyde.

The aldehyde product (189.3 g, 1.02 mole) was suspended in 1 l. of dry dimethylformamide, 350 g of potassium carbonate was added. 145 cc (124 g, 1.54 mole) of dimethyl sulfate was added dropwise over a 20 minute period. After the addition the reaction was heated on the steam bath for 5 minutes. 70 cc of water were added and the reaction was again heated for 5 minutes on the steam bath. The reaction was the poured into ice water and the precipitate was collected. It was crystallized from acetic acid/water (800 cc-50 cc). A second crop was obtained from the mother liquor. Yield 180 g (90%) of 2-chloro-3,4-dimethoxybenzaldehye after drying, m.p. 69°–70°.

The dimethoxybenzaldehyde (180 g, 0.9 mole) was dissolved in 500 cc warm acetic acid. 61 g (0.8 mole) of ammonium acetate was added, followed by 160 cc of nitromethane. The reaction was heated vigorously on the steam bath for 3 hours. Water was then added to the cloud point, while still heating, and the solution was cooled and scratched. The β-nitrostyrene began to oil out and then crystallized. The solution was cooled. The yellow crystals were collected and dried in a vacuum oven. Yield 175 g (80% m.p. 88°–91°) of 2-chloro-3,4-dimethoxy-β-nitrostyrene.

The nitrostyrene (80 g, 0.33 mole) was dissolved in 800 cc of dry tetrahydrofuran. Lithium aluminum hydride, as a 3.7 M solution (260 cc, 0.36 mole), was put in a 5 l. 3 neck flask which had been dried and flushed with argon. It was diluted with 500 cc of dry ether. The solution of the nitrostyrene was added in a thin stream. The flask was cooled in an ice bath so that the heat of reaction caused a gentle reflux on the ether. After addition, the reaction was refluxed one hour, then worked up by adding 36 cc of water, 36 cc of 10% sodium hydroxide and 108 cc of water sequentially and carefully, while cooling the reaction in ice.

The precipitate was collected, washed well with ethyl ether and discarded. The ether-tetrahydrofuran mixture was evaporated.

The above reaction was repeated on 83 g of nitrostyrene. The two crude products were combined and distilled at 0.5 mm to collect at 142°–155° the product containing fraction which was pure 2-(2-chloro-3,4-dimethoxyphenyl)ethylamine by t.l.c. (80 g).

The phenethylamine (25.7 g, 0.12 mole) was heated to 115° in an oil bath. Styrene oxide (14.4 g, 0.12 mole) was added and the reaction was heated for 1 hour. After cooling to ~30°, 2:1 petroleum ether/acetone was added to dissolve the oil; N-[(2-hydroxy-2-phenylethyl)]-N-[2-(2'-chloro-3',4'- dimethoxyphenyl)ethyl]a- mine, crystallized out in 37% yield (15 g) m.p. 100°–101°.

The hydroxyphenethylamine (15 g 0.0445 mole) was dissolved in 60 cc of trifluoroacetic acid and 4.05 cc of concentrated sulfuric acid was added. The reaction was refluxed 2 hours. After cooling most of the trifluoroacetic acid was stripped off and the residue was poured into water. It was made basic with 10% sodium hydroxide and was extracted with ether twice. The ether was dried, and as it was evaporated, a solid separated which was collected; m.p. 115°–121°; 6.0 g of 6-chloro-7,8-dimethoxy-1-phenyl-2,3,4,5-tetrahydro-1H-3-benzazepine. The remaining ether was treated with ethereal hydrogen chloride and the hydrochloride salt precipitated; yield 3.2 g, total 62% m.p. 234°–236°. The dimethoxy derivative was converted to 6-chloro-7,8-dihydroxy-1-phenyl-2,3,4,5-tetrahydro-1H-3-benzazepine hydrobromide using boron tribromide in a 77% yield, m.p. 259°–260°.

EXAMPLE 3

7,8-Dimethoxy-1-phenyl-2,3,4,5-tetrahydro-1H-3-benzazepine (280 g, 0.75 mole) was dissolved in 1700 cc of acetic acid. Bromine (280 g, 1.75 mole) was added in a thin stream. The reaction was stirred for two hours. The precipitate, which formed after 1 hour, was collected and washed with ether. It was dissolved in boiling methanol and acetone was added to destroy the bromine excess. 6-Bromo-7,8-dimethoxy1-phenyl-2,3,4,5-tetrahydro-1H-3-benzazepine hydrobromide was allowed to crystallize from the methanol and a second crop was obtained by adding ether to the mother liquor. Yield 298 g, 77% m.p. 236–238%. This bromination may be applied to any 7,8-dialkoxy or alkanoyloxybenzazepine having a free 6-position.

The hydrobromide was shaken in a mixture of excess 10% sodium hydroxide and methylene chloride. The organic layer was separated, dried and evaporated to give a solid base which was crystallized from toluene-hexane; m.p. 125°–128°, yield 238 g (97%).

The base (12 g, 0.033 mole) was dissolved in 200 cc of methylene chloride and was cooled to −15° C. Boron tribromide (15.4 cc, 16 mole) was added cautiously. The reaction was allowed to run at room temperature for two hours. The solvent was stripped off and the flask was cooled to −15°. Dry methanol was added to destroy the boron tribromide complexes. It was then stripped off. The residue was crystallized from water, then boiled in acetonitrile to aid in the drying of the compound. Yield of 6-bromo-7,8-dihydroxy-1-phenyl-2,3,4,5-tetrahydro-1H-3-benzazepine hydrobromide; 10.26 g. (75%), m.p. 240°–242° after vacuum drying.

Other compounds having a free 6-position and no interfering groups such as unsaturated or aromatic activating centers as known to the art may be similarly brominated.

EXAMPLE 4

6-Bromo-7,8-dimethoxy-1-phenyltetrahydrobenzazepine (13 g, 0.0355 mole) was dissolved in 200 cc of dry acetone. Anhydrous potassium carbonate (10 g, 0.07 mole) was added, followed by 4.2 cc (0.0355 mole) of benzyl bromide. The reaction was refluxed for hours. After cooling, the solid was filtered and the filtrate was stripped off. The resulting oil was dissolved in ether, filtered, and ethereal hydrogen chloride was added. The crystalline precipitate of N-benzyl derivative was filtered and recrystallized from methanol-ether, m.p. 160°–165°.

The solid was then dissolved in methylene chloride and was extracted twice with excess 10% sodium hydroxide. The solvent was dried and evaporated. The residue was dissolved in dry benzene and the benzene was distilled to azeotrope any water present. After repeating the procedure, the oil was pumped under vacuum to remove the benzene. Yield of N-benzyl-6-bromo-7,8-dimethoxy-1-phenyl-2,3,4,5-tetrahydro-1H-3-benzazepine, 12.5 g, 80%.

The 6-bromobenzyl derivative (12.5 g, 0.0277 mole) was converted to its 6-lithium salt which is an important intermediate by reaction with n-butyl lithium in ether. The n-butyl lithium (29 cc, 2.2 M, 0.064 mole) was added via syringe to a 3 neck flask in an argon atmosphere. It was diluted with 3 or 4 volumes of dry ether and cooled to −78° in a dry ice-propanol bath. The benzyl compound was added in 75 cc of dry ether in a thin stream, over a five minute period. The reaction stirred at −78° for five minutes and then 13 g (0.0554 mole) of hexachloroethane was added in 75 cc of ether. The precipitate dissolved immediately.

The reaction mixture was poured into water and the ether layer was retained. The water was extracted again with ether and the ether was dried with magnesium sulfate. Addition of ethereal hydrogen chloride gave a precipitate which was crystallized first from ether-methanol, then from ethyl acetate. Yield of 3-benzyl-6-chloro-7,8-dimethoxy-1-phenyl-2,3,4,5-tetrahydro-1H-3-benzazepine hydrochloride, 9.4 g (80%), m.p. 201°–205°.

This N-benzyl compound (5.33 g, 0.013 mole) was freed from its hydrochloride by extraction into methylene chloride after making alkaline a solution of the hydrochloride. The methylene chloride was dried, evaporated, and the residue dissolved in benzene. It was stripped down to azeotrope any water remaining and the residue was dissolved in 50 cc of dry benzene.

Cyanogen bromide (1.53 g, 0.0144 mole) was dissolved in 50 cc of dry benzene and was warmed to 55°. The N-benzyl compound was added dropwise in benzene and the mixture stirred for 3 hours. The volatiles were stripped off, leaving a solid which was triturated with ether. Yield of N-cyano derivative; 4.0 g (89%), m.p. 149°–151°.

This material (4.0 g, 0.0127 mole) was dissolved in a solution of 50 cc of acetic acid, 6 cc of conc. hydrochloric acid and 31 cc of water. It was heated overnight on the steam bath. The solvents were then stripped off and the residue dissolved in hot methanol. Ether was added and 6-chloro-7,8-dimethoxy-1-phenyl-2,3,4,5-tetrahydro-1H-3-benzazepine hydrochloride crystallized; yield 3.85 g (90%), m.p. 241°–245°.

EXAMPLE 5

The product of Example 4 (3.27 g, 0.0103 mole) was freed from its hydrochloride by making basic its aqueous solution and extracting the mixture with methylene chloride. The solvent was carefully dried and cooled to −15° by a methanol-ice bath. Boron tribromide (4cc) was added and the reaction was stirred at room temperature for 2 hours. The solvent and excess tribromide were stripped and the flask cooled to −78°. Methanol was added cautiously until all the material was dissolved. The methanol was stripped off and the residue crystallized from hot water. The crystals were boiled in dry acetonitrile for an hour, then collected to give 6- chloro-7,8-dihydroxy-1-phenyl-2,3,4,5-tetrahydro-1H-3-benzazepine hydrobromide; (56%), m.p. 259°–260°.

EXAMPLE 6

7,8-Dihydroxy-1-phenyl-2,3,4,5-tetrahydro-1H-3-benzazepine (50 g, 0.17 mole) was suspended in 500 cc of benzene. Trifluoroacetic anhydride (150 g, 0.71 mole) was added dropwise rapidly. All the solid dissolved by the time all the anhydride was added. The solution was stirred an additional hour and then the volatiles were stripped off, leaving the N,O,O-tris-trifluoroacetyl derivative as an oil in quantitative yield. This was added directly to 500 cc of methanol and hydrogen chloride gas was bubbled in for a few minutes. The reaction stirred for 2 hours and then the solvent was stripped off, leaving an oil which was triturated in ether to give 49 g (82%) of 7,8-dihydroxy-1-phenyl-3-trifluoroacetyl-2,3,4,5-tetrahydro-1H-3-benzazepine; m.p. 182°–188°.

The N-acyl compound (5.35 g, 0.015 mole) was suspended in 200 cc of acetic acid. Bromine (1.83 cc, 0.36 mole) was added all at once and the reaction stirred at room temperature 2 hours. It was poured into a beaker containing ice water and sodium bisulfite. The product was extracted from this into ether and was washed with water and then bicarbonate until all the acetic acid was removed. The ether was dried and evaporated. The residue was crystallized from ethyl acetatehexane to give the 6,9-dibromo compound; m.p. 1155°–162°, 4.1 g (54%).

This compound (3.0 g, 0.0059 mole) was dissolved in 100 cc of methanol in a 3 neck flask. 10 cc of 40% sodium hydroxide was put in a pressure compensated addition funnel with an argon inlet tube on top. The flask had a vacuum outlet on it. The entire apparatus was deoxygenated five times by pulling a vacuum and refilling with argon. The alkali solution was added to the solution of dibromo compound and was allowed to stir for ½ hour.

Ethereal hydrogen chloride was then added until the solution was acidic. The entire reaction was stripped down to remove the alcohol and ether. Hot water was added until everything dissolved and then crystallization occurred. 6,9-Dibromo-7,8-dihydroxys-1-phenyl-2,3,4,5-tetrahydro-1H-3-benzazepine hydrochloride was collected and recrystallized from water; 1.24 g (47%), m.p. 205°–207°.

EXAMPLE 7

2-Chloro-3,4-dimethoxyphenethylamine (1.0 g) was reacted with 0.70 g of p-methoxystyrene oxide as described above to give the hydroxyphenethylamine; m.p. 118.5°–121°. This compound (2.16 g) was stirred at room temperature in 15 ml of trifluoroacetic acid with 4 drops of conc. sulfuric acid. Working up as above gave, after purification over a silica gel column with chloroform, 10% methanol/chloroform as eluates, the desired 6-chloro-7,8-dimethoxy-1-p-methoxyphenyl-2,3,4,5-tetrahydro-1H-3-benzazepine (0.87 g).

EXAMPLE 8

The product of Example 7 (0.87 g, 2.50 mmoles) in 25 ml of dry methylene chloride was cooled in an ice-methanol bath as 12.5 ml (25.0 mmoles) of boron tribromide in methylene chloride was added dropwise. After stirring for 4 hours, the mixture was cooled in an ice bath while methanol was carefully added to give 0.37 g, after crystallization from methanol/ethylacetate, of 6-chloro-7,8-dihydroxy-1-p-hydroxyphenyl-2,3,4,5-tetrahydro-1H-3-benzazepine hydrobromide, m.p. 215°.

EXAMPLE 9

Dry dimethylformamide (500 cc) was deoxygenated four times by pulling a vacuum and refilling the vacuated flask with argon. 7,8-Dihydroxy-1-phenyl-3-trifluoroacetyl-2,3,4,5-tetrahydro-1H-3-benzazepine (53.4 g, 0.152 mole) was added and dissolved as the solution and flask were deoxygenated once more. Methylene bromide (52.5 g, 0.3 mole), potassium carbonate (50 g, 0.36 mole) and cupric oxide (1.3 g) were added and the solution was deoxygenated a final time. The reaction was heated at 150° under argon for 2 hours.

It was worked up by pouring into 2 l. of ice water while stirring. The aqueous suspension was extracted 4 times with 300–400 cc ether, and the ether was back extracted 3 times with 1.5 l. water. The ether was dried and evaporated. The residue was dissolved in chloroform and chromatographed on silica gel. Yield of 7,8-methylenedioxy-1-phenyl-3-trifluoroacetyl-2,3,4,5-tetrahydro-1H-3-benzazepine; 35.3 g (64%), m.p. 94°–96° from cyclohexane.

This compound (31.8 g, 0.0876 mole) was dissolved in 105 cc of acetic acid and bromine (4.86 cc, 0.089 mole) was added all at once. The reaction stirred at room temperature overnight. The flask was then cooled and the solid was collected. The mother liquors were warmed, diluted with water and then allowed to cool. A second crop was collected. To the mother liquor was added a small amount more of bromine. It stirred for two days at room temperature and the relatively small amount of precipitate was collected. The crude material was recrystallized from acetic acid to give 28 g (72%) of the 6-bromo compound, m.p. 160°–165°.

The 6-bromo compound (28 g) was suspended in 250 cc of methanol, 50 cc of 40% sodium hydroxide was added and the reaction mixture was heated to boiling. The mixture was then stirred for one hour. The methanol was stripped off and water and ether were added to the residue. The layers were shaken, separated and the water was washed again with ether. The ether layers were dried and ethereal hydrogen chloride was added. The precipitate was recrystallized from methanol-ether acetate to give 6-bromo-7,8-methylenedioxy-1-phenyl-2,3,4,5-tetrahydro-1H-3-benzazepine hydrochloride, 21.3 g (88%), m.p. 240–248.

EXAMPLE 10

A mixture of 4.5 g of 6-chloro-7,8-dimethoxy-1-phenyl-2,3,4,5-tetrahydro-1H-3-benzazepine, 0.02 ml of n-butyl bromide and 0.02 mol of potassium hydroxide is dissolved in 120 ml of dry methanol and refluxed for 48 hours. The reaction mixture is evaporated to dryness, taken up in ethyl acetate and filtered to remove inorganic salts. The filtrate is washed with water, dried and evaporated to give 3-n-butyl-6-chloro-7,8-dimethoxy-1-phenyl-2,3,4,5-tetrahydro-1H-3-benzazepine.

The 3-n-butyl benzazepine (0.01 mol) is dissolved in 120 ml of dry methylene chloride and 0.032 mol of boron tribromide is added dropwise at −10° C. The solution is warmed to room temperature and stirred for two hours. The excess boron tribromide is destroyed with methanol added dropwise with ice-cooling. The cold solution is refluxed on the steam bath to remove hydrogen bromide and then evaporated to yield 3-n-butyl-6-chloro-7,8-dihydroxy-1-phenyl-2,3,4,5-tetrahydro-1H-3-benzazepine hydrobromide.

EXAMPLE 11

A mixture of 9.7 g of sodium hydride, 38 g of trimethylsulfonium iodide and 25.2 g (0.185 mol) of o-methoxybenzaldehyde is reacted to give o-methoxystyrene oxide.

A mixture of 34 g of 2-chloro 3,4-dimethoxy-phenylethylamine and 28 g of o-methoxystyrene oxide is heated with stirring under argon on a steam bath overnight. Chilling and stirring yields the product N-[2-(2-chloro-3,4-dimethoxyphenyl)ethyl]-2-hydroxy-2-(2-methoxyphenyl)ethylamine.

A solution of 5 g of the above prepared ethylamine in 35 ml of 48% hydrobromic acid is heated at reflux under argon for two hours. The reaction mixture is evaporated and the hydrobromide salt is converted to the free base using bicarbonate and carbonate to pH 8.5 in water. The aqueous solution is extracted with ethyl acetate, the extract is dried and evaporated to give the free base. The latter is dissolved in methanol and treated with ethereal hydrogen chloride to give 6-chloro-7,8-dihydroxy-1-(2-hydroxyphenyl)-2,3,4,5-tetrahydro-1H-3-benzazepine hydrochloride.

EXAMPLE 12

A 5.20 g sample of 6-bromo-7,8-dihydroxy-1-phenyl-2,3,4,5-tetrahydro-1H-3-benzazepine free base is slurried in 100 ml of 1:1 methanol-acetone. The slurry is stirred under nitrogen and chilled to about 0°. Sodium bicarbonate (1.68 g, 0.020 mol) is added as a solid and to the stirred mixture is added 5.69 g (0.040 mol) of methyl iodide in 60 ml of acetone, dropwise over a two to three hour period. After addition is completed the mixture is allowed to warm to ambient temperature and stirred for about 40 hours. The reaction mixture is filtered and the filtrate is concentrated to yield additional solid. The combined solids are slurried in water to remove inorganic salts, filtered and the solid dried to give 6-bromo-7,8-dihydroxy-3,3-dimethyl-1-phenyl-2,3,4,5-tetrahydro-1H-3-benzazepinium iodide.

EXAMPLE 13

A 3.9 g sample of 6-chloro-7,8-dihydroxy-1-phenyl-2,3,4,5-tetrahydro-1H-3-benzazepine is slurried in 25 ml of acetone and 0.7 g (0.016 mol, 10% excess) of ethylene oxide is added. The mixture is placed in a pressure bottle and stirred at ambient temperature for about 40 hours. The reaction mixture is then heated to 60°–80° for 30 minutes, cooled and filtered. Concentration of the filtrate gives a solid which is taken up in ethyl acetate and reprecipitated with ether. The solid thus obtained is dissolved in ethanol and treated with ethereal hydrogen chloride to give 6-chloro-7,8-dihydroxy-3-(2-hydroxyethyl)-1-phenyl-2,3,4,5-tetrahydro-1H-3-benzazepine hydrochloride.

EXAMPLE 14

A mixture of 42.0 g of 57% sodium hydroxide dispersed in oil and 700 ml of dimethyl sulfoxide is stirred at 70°–75° for one to one and one-half hours. The solution in diluted with 700 ml of dry tetrahydrofuran and cooled to 0°, under nitrogen. A 200 g of (1.0 mol) sample of trimethylsulfonium iodide is added in portions, maintaining the temperature between 0°–5°. The mixture is stirred for 15 minutes and then a solution of 70.4 g (0.50 mol) of o-chlorobenzaldehyde in 300 ml of dry tetrahydrofuran is added dropwise. The resulting mixture is stirred at room temperature for four hours, poured into water and extracted with ether. The extract is washed with brine, dried and evaporated in vacuo to leave o-chlorostyrene oxide.

A solution of 27.5 g of N-benzyl-2-chloro-3,4- dimethoxyphenylethylamine and 23.3 g (0.15 ml) of m-chlorostyrene oxide in 500 ml of methanol is stirred and refluxed overnight. The methanol is removed in vacuo and the residual N-benzyl-N-[2-(2-chloro-3,4-dimethoxyphenyl)ethyl]-2-hydroxy-2-(2-chlorophenyl)ethylamine is reduced without further purification. This sample (0.01 mol) is dissolved in ether, acidified with ethereal hydrogen chloride and the hydrochloride precipitates. The latter is dissolved in 90 ml of methanol, the solution is added to a mixture of 0.5 g of palladium-on-charcoal in 10 ml of ethyl acetate and the mixture is hydrogenated at room temperature for 90 minutes at 60 psi. The reaction mixture is filtered and the filtrate evaporated in vacuo to yield N-[2-(2-chloro-3,4-dimethoxyphenyl)ethyl]-2-hydroxy-2-(2-chlorophenyl)ethylamine hydrochloride.

A solution of 6.0 g (0.0161 mol) of the above prepared compound in 250 ml of 48% hydrobromic acid is stirred and refluxed for three hours. The reaction mixture is evaporated in vacuo to give 6-chloro-1-(2-chlorophenyl)-7,8-dihydroxy-2,3,4,5-tetrahydro-1H-3-benzazepine hydrobromide.

EXAMPLE 15

Following the procedure of Example 14 and employing 42.0 g of 57% of sodium hydride in mineral oil, 200 g (0.1 mol) of trimethylsulfonium iodide and 70.4 g (0.50 mol) of o-bromo-benzaldehyde there is obtained o-bromostyrene oxide.

Similarly 2.71 g of N-benzyl-2-chloro-3,4-dimethoxy-phenethylamine and 2.33 g (0.015 mol) of o-bromostyrene oxide are reacted in methanol to give N-benzyl-N-[2-(2-chloro-3,4-dimethoxyphenyl)ethyl]-2-hydroxy-2-(2-bromophenyl)ethylamine. The latter is converted to its hydrochloride, which is dissolved in 90 ml of methanol and hydrogenated over 1 g of 10% palladium-on-carbon in 10 ml of ethyl acetate at room temprature for six hours. The reaction mixture is filtered and evaporated in vacuo to leve N-[2-(2-chloro-3,4-dimethoxyphenyl)ethyl]-2-hydroxy-2-(2-bromophenyl)ethylamine hydrochloride.

A solution of 4.0 g of the above hydrochloride in 250 ml of 48% hydrobromic acid is stirred and refluxed for two hours. The reaction mixture is evaporated in vacuo to yield 6-chloro-1-(2-bromophenyl)-7,8-dihydroxy-2,3,4,5-tetrahydro-1H-3-benzazepine hydrobromide.

Substituting trifluoromethyl, fluoro, methyl, ethyl, ethoxystyrene oxides will give the compounds of this invention whose structures include the corresponding substituted 1-phenyl moieties.

EXAMPLE 16

A solution of 3.7 g of 6-chloro-7,8-dimethoxy-1-phenyl-2,3,4,5-tetrahydro-1H-3-benzazepine in 15 ml of formic acid and 10 ml of formaldehyde is refluxed for 18 hours. The reaction mixture is evaporated to dryness, 20 ml of 6N hydrochloric acid is added and the solution is again evaporated to dryness to give a liquid. The latter is treated with 20 ml of 10% sodium hydroxide solution and the mixture is extracted with ether. The dried extract is evaporated to give 6-chloro-7,8-dimethoxy-3-methyl-1-phenyl-2,3,4,5-tetrahydro-1H-3-benzazepine.

The above prepared 3-methyl benzazepine (2.6 g) is dissolved in 120 ml of dry methylene chloride and 6.8 g (0.027 mol) of boron tribromide is added dropwise at −10°. The resulting solution is warmed at room temperature and stirred for two hours. The excess boron tribromide is destroyed with methanol, added dropwise with ice-cooling. The solution is refluxed on the steam bath to remove hydrogen bromide and then evaporated to dryness to furnish 6-chloro-7,8-dihydroxy-3-methyl-1-phenyl-2,3,4,5-tetrahydro-1H-3-benzazepine hydrobromide, 247°–249°.

EXAMPLE 17

A 4.0 g sample of 3-benzyl-6-chloro-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-6-chloro-7,8-diacetoxy-1-phenyl-2,3,4,5-tetrahydro-1H-3-benzazepine hydrochloride.

The diacetoxy compound prepared above, 3.5 g is dissolved in 100 ml of ethanol and 1 g of 10% palladium-on-carbon is added. The mixture is hydrogenated in a Parr apparatus at 50° under 50 psi of hydrogen for one hour. The reaction mixture is filtered and the filtrate is evaporated to give 6-chloro-7,8-diacetoxy-1-phenyl-2,3,4,5-tetrahydro-1H-3-benzazepine hydrochloride.

Alternatively 6-chloro-7,8-dihydroxy-1-phenyl-2,3,4,5-tetrahydro-1H-3benzazepine hydrobromide (10 g) is dissolved in trifluoroacetic acid and reacted with a stoichiometric amount of acetyl chloride at room temperature. The next day the reaction mixture is evaporated and the residue recrystallized to give the desired diacetoxy derivative.

Substituting other alkanoyl ahydrides or chlorides gives various 7,8-alkanoyl derivatives.

EXAMPLE 18

Using N-alkylation procedures described above but using 6-chloro-7,8-dimethoxy-1-phenyl-2,3,4,5-tetrahydro-1H-3-benzazepine as a model compound the N-allyl, N-butyl, N-amyl or N-2,2-dimethylallyl derivatives are prepared. Hydrolysis of the methoxy groups as described gives the more active 6-chloro-7,8-dihydroxy compounds.

EXAMPLE 19

Substituting a stoichiometric quantity of 2-fluoro-3,4-dimethoxyphenethyl amine in the synthetic procedures of Example 2 gives 6-fluoro-7,8-dimethoxy-1-phenyl-2,3,4,5-tetrahydro-1H-3-benzazepine. Hydrolysis with boron tribromide as in Example 2 gives 6-fluoro-7,8-dihydroxy-1-phenyl-2,3,4,5-tetrahydro-1H-3-benzazepine. Substituting 2-trifluoromethyl-3,4-dimethoxyphenethylamine, prepared via 2-trifluoromethyl-3,4-dimethoxytoluene, in Example 2 gives 6-trifluoromethyl-7,8-dimethoxy-1-phenyl-2,3,4,5-tetrahydro-1H-3-benzazepine then hydrolysis with boron tribromide gives 6-trifluoromethyl-7,8-dihydroxy-1-phenyl-2,3,4,5-tetrahydro-1H-3-benzazepine.

EXAMPLE 20

A mixture of 4.84 g of 50% sodium hydride in mineral oil and 70 ml of dry dimethylsulfoxide was stirred at 65°–70° for 80 minutes. After dilution with 70 ml of dry tetrahydrofuran, the mixture was cooled to 0° while a solution of 19.0 g (0.093 mole) of trimethylsulfonium iodide in 100 ml of dimethylsulfoxide was added. A solution of 12.6 g (0.0928 mole) of m-anisaldehyde in 40 ml of tetrahydrofuran was quickly added. After stirring for 15 minutes at 0° and 1¼ hour at 25°, the mixture is poured into 1½ l. of ice/water slurry and extracted well with water. The combined organic layers were washed with brine, dried and concentrated to give 13 g of crude epoxide. This is mixed with 13.0 g of 2-(2-chloro-3,4-dimethoxyphenyl) ethylamine and heated at 110° for 4 hours. The product was chromatographed over silica gel with 3% methanol/chloroform. The product containing cuts were worked up to give 1.9 g of N-[2-(2-chloro-3,4-dimethoxyphenyl)ethyl]-2-hydroxy-2-(m-methoxyphenyl)ethylamine, m.p. 95.5°–96.5°.

The p-chlorophenyl congener melted at 99°–100°. The p-methylphenyl congener melted at 117°–118°.

The m-methoxy substituted hydroxyphenethylamine intermediate (1.7 g) in 25 ml of 48% hydrogen bromide solution was heated at 135°–140° for 3 hours. The solvent was evaporated in vacuo and the residue dissolved in methyl alcohol/2-propanol. After charcoal treatment, the solvent was evaporated to leave an amber syrup. This was taken into acetonitrile/2-propanol and a white solid separated by addition of ether. Recrystallization from acetonitrile/ether gave 1.2 g of 6-chloro-7,8-dihydroxy-1-(m-hydroxyphenyl)-2,3,4,5-tetrahydro-1H-3-benzazepine hydrobromide m.p. 195°–200°.

The p-chlorophenyl congener melted at 243°–246°. The p-methylphenyl congener melted at 250°–253°.

EXAMPLE 21

A mixture of 8.0 g of 2-chloro-3,4-dimethoxy-phenethylamine and 5.25 g of m-trifluoromethyl-α-methoxyphenethylbromide is heated at 100°–105° for 2½ hours. The product was partitioned betwen ethyl acetate and 5% sodium bicarbonate solution. The organic layer was removed, washed with brine, dried and concentrated. The residue was passed over 350 g of silica gel with 1 to 2% methanol/chloroform. The resulting product was an oil whose hydrochloride melted at 200°–202°. The oily base (2.5 g.) was heated with 50 ml of 48% hydrogen bromide and worked up as above to give the desired 6-chloro-7,8-dihydroxy-1-(m-trifluoromethylphenyl)-2,3,4,5-tetrahydro-1H-3-benzazepine hydrobromide, m.p. ~250°.

6-Bromo-7,8-dimethoxy-1-phenyl-3-trifluoroacetyl-2,3,4,5-tetrahydro-1H-3-benzazepine (5 g, prepared by reaction of trifluoroacetic anhydride in benzene on the N-hydrogen compound) is reacted with an excess of butyl lithium in ether as in Example 4 to give the 6-lithium salt-3-butyl-lithium adduct. This intermediate is reacted without isolation with iodine. After hydrolysis with water, 6-iodo-7,8-dimethoxy-1-phenyl-2,3,4,5-tetrahydro-1H-3-benzazepine is obtained. This compound is treated with boron tribromide as in Example 3 to give the 7,8-dihydroxy derivative.

2-Chloro-3-hydroxy-4-methoxybenzaldehyde is treated with hydrogen bromide to give 2-chloro-3,4-dihydroxybenzaldehyde which is converted to the methylenedioxy derivative with dibromomethane as described above. The product is condensed with nitromethane and the resulting nitroethylene reduced to give the phenethylamine. This compound is condensed with p-methoxystyrene oxide to give the α-hydroxyphenethylamine intermediate which is reated with an excess of trifluoroacetic acid at room temperature for 18 hours to give 6-chloro-7,8-methylenedioxy-1-phenyl-2,3,4,5-tetrahydro-1H-3-benzazepine. This compound is split using boron trichloride as described above to give 6-chloro-7,8-dihydroxy-1-p-methoxyphenyl-2,3,4,5-tetrahydro-1H-3-benzazepine.

EXAMPLE 22

| Ingredients | Mg. per Capsule |
| --- | --- |
| 6-Chloro-7,8-dihydroxy-1-phenyl-2,3,4,5-tetrahydro-1H-3-benzazepine (as an acid addition salt) | 125 (free base) |
| Magnesium stearate | 2 |
| Lactose | 200 |

The above ingredients are thoroughly mixed and placed into hard gelatin capsules. Such capsules are administered orally to subjects in need of treatment from 1–5 times daily to induce dopaminergic activity.

EXAMPLE 23

| Ingredients | Mg. per Tablet |
| --- | --- |
| 6-Chloro-7,8-dihydroxy-1-phenyl-2,3,4,5-tetrahydro-1H-3-benzazepine (as an acid addition salt) | 200 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into tablets.

The capsules or tablets thusly prepared are administered orally to an animal or human requiring stimulation of either central or peripheral dopamine receptors within the dose ranges set forth hereinabove. Similarly other compounds of Formula I and the illustrative examples can be formulated in the same manner to give pharmaceutical compositions useful in the methods of this invention based on the chemical characteristics and relative biological activity using the test methods outlined.

What is claimed is:

1. The method of preparing a 6-bromo-7,8-dimethoxy-1-phenyl-2,3,4,5-tetrahydro-1H-3-benzazepine hydrobromide comprising the step of reacting a 6-hydrogen-7,8-dimethoxy-1-phenyl-2,3,4,5-tetrahydro-1H-3-benzazepine with about two mole equivalents of bromine in acetic acid at ambient temperature.

* * * * *